(12) United States Patent
Marti et al.

(10) Patent No.: US 9,873,010 B2
(45) Date of Patent: *Jan. 23, 2018

(54) RANGE OF MOTION IMPROVEMENT DEVICE

(71) Applicants: Eduardo M. Marti, Sunrise, FL (US); Robert T. Kaiser, South Hampton, NJ (US)

(72) Inventors: Eduardo M. Marti, Sunrise, FL (US); Robert T. Kaiser, South Hampton, NJ (US)

(73) Assignee: T-Rex Investment, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 15/612,541

(22) Filed: Jun. 2, 2017

(65) Prior Publication Data

US 2017/0266476 A1    Sep. 21, 2017

Related U.S. Application Data

(63) Continuation of application No. 14/730,574, filed on Jun. 4, 2015, now Pat. No. 9,669,249.

(Continued)

(51) Int. Cl.
*A63B 21/00* (2006.01)
*A63B 71/06* (2006.01)
(Continued)

(52) U.S. Cl.
CPC ...... *A63B 21/00069* (2013.01); *A61B 5/1114* (2013.01); *A61B 5/1121* (2013.01); *A61B 5/4585* (2013.01); *A61B 5/6828* (2013.01); *A61B 5/6835* (2013.01); *A61H 1/024* (2013.01); *A61H 1/0244* (2013.01); *A63B 21/00178* (2013.01); *A63B 21/00181* (2013.01); *A63B 21/4011* (2015.10); *A63B 21/4031* (2015.10); *A63B 23/0405* (2013.01); *A63B 23/0482* (2013.01); *A63B 23/0494* (2013.01); *A63B 24/0087* (2013.01); *A63B 71/0622* (2013.01); *G05G 9/047* (2013.01); *A61B 5/22* (2013.01); *A61B 5/6831* (2013.01); *A61B 5/6894* (2013.01); *A61B 5/6895* (2013.01); *A61B 2505/09* (2013.01); *A61H 2201/0149* (2013.01);

(Continued)

(58) Field of Classification Search
CPC ............... A63B 21/00; A63B 24/0062; A63B 23/03541; A63B 21/00069; A63B 24/0075; A63B 2023/006; A63B 23/00; A63B 23/04; A63B 23/0494; A63B 24/00; A63B 21/00058; A63B 21/008
USPC .............................................. 482/139; 601/5
See application file for complete search history.

(56) References Cited

U.S. PATENT DOCUMENTS 4,185,818 A * 1/1980 Brentham .......... A63B 21/0083
                                                        482/112
4,407,496 A * 10/1983 Johnson ............. A63B 23/0494
                                                        482/139

(Continued)

*Primary Examiner* — Andrew S Lo
(74) *Attorney, Agent, or Firm* — Robert M. Schwartz; Alfred K. Dassler

(57) ABSTRACT

An end range of motion improving device is disclosed including, first and second link members to independently rotate an upper leg and a lower leg of a patient, having a controller to selectively rotate the link members, and a networked computing system to facilitate communication between the controller and other networked devices.

7 Claims, 12 Drawing Sheets

Related U.S. Application Data

(60) Provisional application No. 62/134,633, filed on Mar. 18, 2015, provisional application No. 62/042,399, filed on Aug. 27, 2014, provisional application No. 62/007,541, filed on Jun. 4, 2014.

(51) Int. Cl.
| | |
|---|---|
| *A63B 23/04* | (2006.01) |
| *A63B 24/00* | (2006.01) |
| *G05G 9/047* | (2006.01) |
| *A61B 5/00* | (2006.01) |
| *A61B 5/11* | (2006.01) |
| *A61H 1/02* | (2006.01) |
| *A63B 23/035* | (2006.01) |
| *A63B 23/00* | (2006.01) |
| *A63B 71/00* | (2006.01) |
| *A61B 5/22* | (2006.01) |
| *A63B 21/002* | (2006.01) |

(52) U.S. Cl.
CPC .......... *A61H 2201/0176* (2013.01); *A61H 2201/0192* (2013.01); *A61H 2201/1215* (2013.01); *A61H 2201/1642* (2013.01); *A61H 2201/1676* (2013.01); *A61H 2201/501* (2013.01); *A61H 2201/5043* (2013.01); *A61H 2201/5061* (2013.01); *A61H 2201/5069* (2013.01); *A61H 2201/5076* (2013.01); *A61H 2201/5097* (2013.01); *A61H 2203/0431* (2013.01); *A61H 2205/102* (2013.01); *A63B 21/0023* (2013.01); *A63B 21/4047* (2015.10); *A63B 23/03508* (2013.01); *A63B 2023/006* (2013.01); *A63B 2024/0068* (2013.01); *A63B 2071/0018* (2013.01); *A63B 2071/0081* (2013.01); *A63B 2071/065* (2013.01); *A63B 2071/0647* (2013.01); *A63B 2208/0233* (2013.01); *A63B 2220/16* (2013.01); *A63B 2220/17* (2013.01); *A63B 2220/51* (2013.01); *A63B 2225/093* (2013.01); *A63B 2225/50* (2013.01); *G08C 2201/42* (2013.01)

(56) References Cited

U.S. PATENT DOCUMENTS

| | | | | |
|---|---|---|---|---|
| 4,441,708 A * | 4/1984 | Brentham | ........ | A63B 23/03516 482/112 |
| 4,502,681 A * | 3/1985 | Blomqvist | ........... | A63B 21/04 482/130 |
| 4,566,692 A * | 1/1986 | Brentham | ......... | A63B 21/0083 482/113 |
| 4,628,910 A * | 12/1986 | Krukowski | ........ | A63B 21/0058 482/5 |
| 4,691,694 A * | 9/1987 | Boyd | ................ | A63B 21/0058 482/5 |
| 4,718,665 A * | 1/1988 | Airy | ..................... | A63B 21/015 482/119 |
| 4,776,587 A * | 10/1988 | Carlson | .............. | A63B 23/0494 482/134 |
| 4,905,676 A * | 3/1990 | Bond | .................... | A63B 24/00 482/6 |
| 5,020,797 A * | 6/1991 | Burns | ................ | A63B 23/0494 482/137 |
| 5,209,223 A * | 5/1993 | McGorry | ......... | A63B 21/00178 482/100 |
| 5,280,783 A * | 1/1994 | Focht | ................... | A61H 1/0259 601/34 |
| 5,403,251 A * | 4/1995 | Belsito | .................. | A63B 24/00 345/173 |
| 5,486,150 A * | 1/1996 | Randolph | ........ | A63B 21/00072 482/123 |
| 5,980,435 A * | 11/1999 | Joutras | ................. | A43B 1/0054 482/114 |
| 6,010,434 A * | 1/2000 | Hodges | .............. | A63B 21/0552 482/129 |
| 6,056,675 A * | 5/2000 | Aruin | ................. | A63B 21/0023 482/140 |
| 6,872,187 B1 * | 3/2005 | Stark | ..................... | A61F 5/0102 482/8 |
| 7,695,416 B2 * | 4/2010 | Weiner | .................. | A61H 1/024 482/112 |
| 7,963,932 B2 * | 6/2011 | Ashihara | .............. | A61F 5/0102 601/35 |
| 8,333,722 B2 * | 12/2012 | Ewing | .................... | A61H 1/024 482/907 |
| 2005/0272575 A1 * | 12/2005 | Melegati | ............ | A63B 21/0552 482/110 |
| 2005/0273022 A1 * | 12/2005 | Diaz | ..................... | A61H 1/0259 601/5 |
| 2010/0130893 A1 * | 5/2010 | Sankai | ............... | A63B 21/4047 601/5 |
| 2010/0227741 A1 * | 9/2010 | Rosenberg | ........... | A61F 5/0123 482/79 |
| 2012/0232438 A1 * | 9/2012 | Cataldi | ................ | A61H 1/0259 601/5 |
| 2013/0204168 A1 * | 8/2013 | Bombard | ............. | A61H 1/0244 601/5 |
| 2013/0245524 A1 * | 9/2013 | Schofield | .............. | A61F 5/0125 602/16 |
| 2014/0094721 A1 * | 4/2014 | Diallo | .................... | A61H 1/024 601/5 |
| 2015/0051520 A1 * | 2/2015 | Donohue | ............... | A61H 1/005 601/35 |
| 2015/0190249 A1 * | 7/2015 | Ishibashi | .................. | A61H 3/00 623/24 |
| 2015/0265428 A1 * | 9/2015 | Akiba | ...................... | A61F 2/72 700/275 |
| 2015/0297934 A1 * | 10/2015 | Agrawal | ................ | A61H 1/0266 482/4 |
| 2015/0351990 A1 * | 12/2015 | Ewing | .................... | A61H 1/024 601/5 |

* cited by examiner

RANGE OF MOTION IMPROVEMENT DEVICE

CROSS-REFERENCE TO RELATED APPLICATIONS

This application is a continuation application of U.S. patent application Ser. No. 14/730,574, filed Jun. 4, 2015, entitled "Range of Motion Improvement Device", which claims the benefit of U.S. Provisional Application Ser. No. 62/007,541, filed on Jun. 4, 2014, entitled A Powered Knee Exerciser, U.S. Provisional Application Ser. No. 62/042,399, filed on Aug. 27, 2014, entitled 3 Axis Actuator Driven Therapy Shoulder Device, and U.S. Provisional Application Ser. No. 62/134,633, filed on Mar. 18, 2015, entitled Knee and Shoulder Exercisers, the prior applications are herewith incorporated by reference in their entirety.

BACKGROUND OF THE INVENTION

Following certain injuries, surgery or other medical treatments that affect the mobility of the knee, it is customary for the patient to be prescribed physical therapy. For example after knee operation, scar tissue may form in knee tissue (i.e. arthrofibrosis) and as such, mobility of the knee may suffer. For example, without rehabilitative therapy, a patient who has undergone knee surgery may not be able to walk properly or return to independent daily activities and could potentially suffer from back pain, hip pain, and knee pain.

Normal range of motion of the knee is considered to be 0° of extension and 135° degrees of flexion. For example, 0° of extension may be achieved by a person extending their knee such that their lower leg is parallel with their upper leg. An upper leg of a patient is also known as a thigh, and is defined as the area between a patient's pelvis and knee. For example, the upper leg usually includes the femur. On the other hand, a lower leg of a patient is defined as the part of the leg that lies between the knee and the ankle. The lower leg usually includes the fibula and the tibia. As another example, 135° of flexion can be achieved when a person flexes their lower leg such that an angle subtending their lower leg and their upper leg is 45°. Knee extension describes straightening of the lower leg relative to the upper leg, and knee flexion describes bending the knee such that an angle between the lower leg and the upper leg decreases. Hip extension described straightening the upper leg relative to the spine, and flexion is described as bending the hip joint such that the upper leg to spine angle decreases.

FIELD OF THE INVENTION

The present invention relates to knee range of motion therapy, and more particularly to a knee range of motion therapy device.

DESCRIPTION OF THE RELATED ART

Commonly, a physician may prescribe therapeutic exercises to help a patient regain normal knee flexion and extension ranges, otherwise known as range of motion. For example, a therapist may prescribe active range of motion (AROM) exercises, active assisted Range of Motion (AAROM) exercises, passive range of motion (PROM) exercises, and/or progressive resisted exercises (PRE) to help strengthen muscles surrounding the knee and break down scar tissue. AROM is defined as moving a body part without assistance of another. AAROM is defined as moving a body part with the assistance of another. PROM is defined as moving a body part with only the assistance of another. PRE are defined as movement of a body part against or opposing outside resistance.

As an example, to increase range of motion in the knee, a physical therapist may apply passive range of motion therapy. For example, to increase flexion range of the knee, the therapist may manually pull the patient's foot toward the patient's body, increasing a flexion angle of the knee. After a desired flexion is achieved, the therapist may return the patient's foot to the original position to complete a cycle. Such therapy is applied on a frequent basis and maximum extension and flexion angles are measured to quantify progress.

However, such manual methods are inconvenient because either the therapist or the patient has to travel on a frequent basis, possibly for many months. As such, knee therapy via a physical therapist is time-consuming, inefficient and costly.

Efforts may be made to train others, for example, the wife or husband of the patient, to perform these exercises. However, such training efforts have poor results, however, due to lack of patient and caregiver compliance and insufficient training to replicate the skill of a licensed therapist.

Such issues with manual methods have led to development of machines that attempt to reproduce the capabilities of a licensed physical therapist, allowing therapy to be provided without requiring the patient or a therapist to travel and spend time providing therapy. For example, a therapy machine may be provided to a patient so that the patient may engage in therapy by themselves. However, current knee range of motion therapy machines have various problems. Common knee range of motion therapy machines merely apply a translational force to the foot of a patient via a horizontal track system. Other common knee range of motion machines require two separate machines for flexion and extension, respectively.

As such, common knee range of motion machines are not able to rotate a knee of a patient independently from a hip joint of the patient, which may be an issue for patients with hip dysfunction. Further, current range of motion therapy machines place significant translational force on the lower leg of a patient, which applies unnecessary and undesired translational forces on the knee joint. Furthermore, common range of motion therapy machines are not configured to record usage data, which may help track progress or check on patient compliance. Even further, current range of motion therapy machines are not able to concurrently and safely provide the above described active and passive range of motion therapy modalities, because common machines are not able to anatomically match a rotational axes of a patient's leg so that a patient may apply anatomically matched rotational forces, or the machines require an inconvenient hand crank to assist the passive or active motions.

Therefore, there exists a need for a knee range of motion therapy machine or device that can rotate a knee of a patient independently from a hip of the patient, provide both active and passive range of motion therapies and record usage data to track progress and check patient compliance.

SUMMARY OF THE INVENTION

Disclosed is an end range of motion improving device comprising a frame, the frame including, a first link member configured for being secured to an upper leg of a patient and configured for rotating the upper leg of the patient about a hip axis of the patient through a predetermined upper leg range of motion, a second link member configured for being secured to a lower leg of the patient and for rotating the lower leg of the patient about a knee axis of the patient through a predetermined lower leg range of motion and at least one actuator for rotating the first link member about the hip axis and for rotating the second link member about the knee axis, and a controller controlling the at least one actuator for selectively rotating the first link member about the hip axis through the predetermined upper leg range of motion and selectively rotating the second link member about the knee axis through the predetermined lower leg range of motion.

In another aspect, the frame includes an attachment means to attach a seat.

In another aspect, the first link member includes an upper leg support to rotate the upper leg of the patient about the hip axis.

In another aspect, the second link member includes a lower leg support to rotate the lower leg of the patient about the knee axis.

In another aspect, the first link member rotates about a first axis provided by a first axis assembly to rotate the upper leg and the second link member rotates about a second axis provided by a second axis assembly to rotate the lower leg.

In another aspect, at least one of the first axis assembly and the second axis assembly includes a hinge system.

In another aspect, at least one of the first axis assembly and the second axis assembly includes a gear system.

In another aspect, the second axis assembly links the first link member to the second link member.

In another aspect, the first axis assembly links a base of the frame to the first link member.

In another aspect, the first link member independently rotates about the first axis without causing the second link member to rotate about the second axis, and the second link member independently rotates about the second axis without causing the first link member to rotate about the first axis.

In another aspect, the frame includes one or more adjustment means to anatomically match the first axis to the hip axis and the second axis to the knee axis.

In another aspect, the base includes wheels to wheel the frame across a surface on which the base rests.

In another aspect, the gear system includes a polycentric gear system.

In another aspect, the controller registers usage data.

In another aspect, the usage data includes time that at least one of the first and second link members have spent at a particular angle.

In another aspect, the usage data includes a current angle of at least one of the first and second link members.

In another aspect, the usage data includes a maximum and minimum angle reached by at least one of the first and second link members.

In another aspect, the usage data includes force data from forces applied to at least one of the first and second link members.

In another aspect, the controller sets rotation limits for at least one of the first link member and second link member.

In another aspect, the controller sets force limits for at least one of the first link member and second link member.

In another aspect, the controller is set to shut down after a predetermined shut down time via user input.

In another aspect, the controller is set to hold for a predetermined pause time at least one of the upper leg and second link member at an angle at which either the rotation limit or the force limit is registered by the control module.

In another aspect, the controller is set to cause at least one of the first link member and second link member to automatically rotatably cycle between at least one of the force limit and rotation limits for a predetermined number of cycles, and the control module registers the number of cycles executed.

In another aspect, the usage data includes the number of cycles executed.

In another aspect, the controller is set to automatically rotatably cycle the upper and/or second link member between at least one of limits in increments of rotation while holding an angle at each increment for a predetermined increment pause time set by the control module.

In another aspect, the control module includes a display configured to read out one or more of the usage data, force limit, rotation limits, shut down time, pause time, predetermined number of cycles, executed number of cycles, and increment pause time.

In another aspect, the usage data, force limit, rotation limits, shut down time, pause time, predetermined number of cycles, executed number of cycles, and increment pause time is reported to a server via a computer network.

In another aspect, the controller is controllable via a remote device through a computer network.

BRIEF DESCRIPTION OF THE DRAWINGS

It is to be understood that in the drawings, like reference numbers indicate like elements.

DESCRIPTION OF THE PREFERRED EMBODIMENTS

Figure 1:
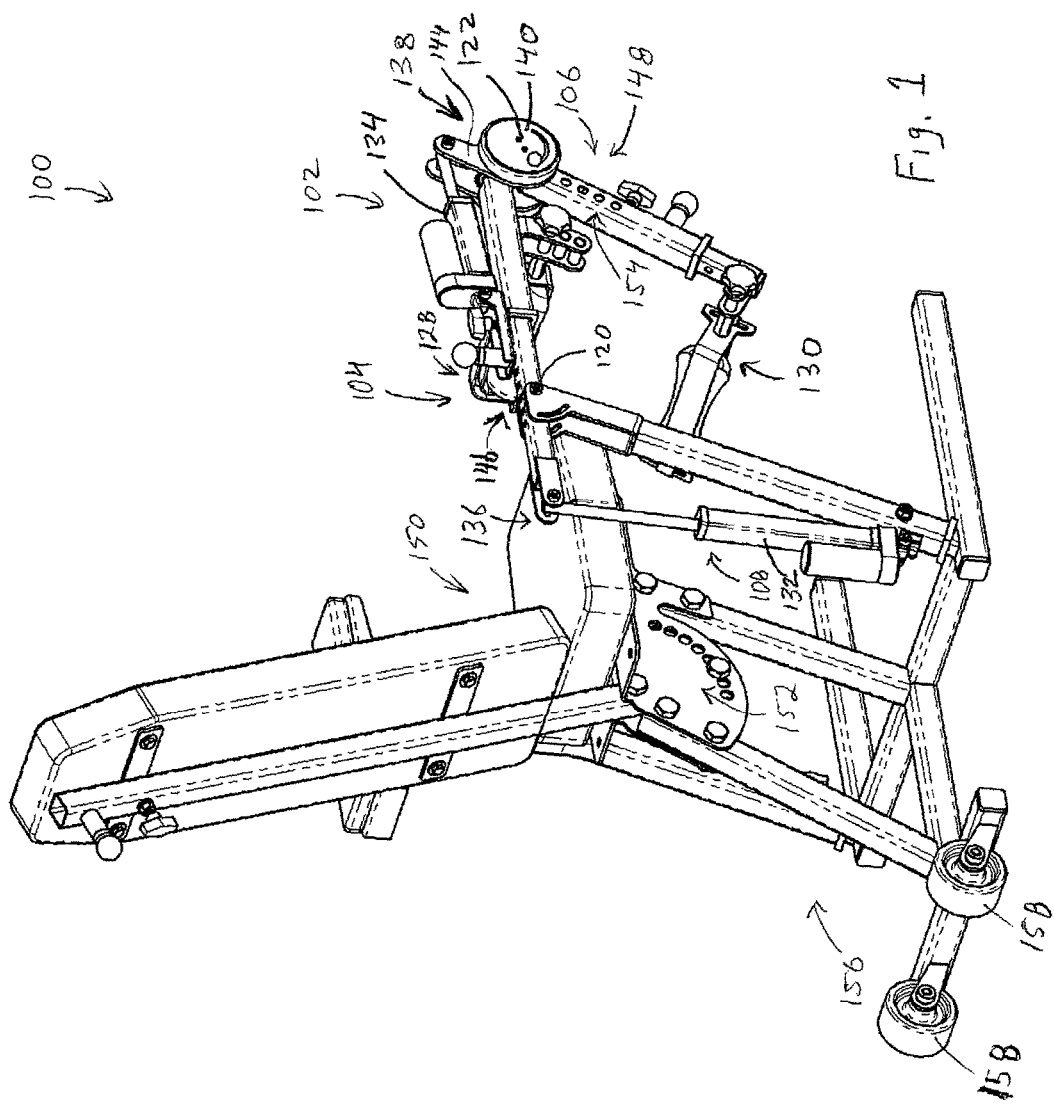
FIG. 1 is an isometric back view of an end range of motion improving device.

FIG. 1 shows a first embodiment of an end range of motion improving device 100. Particularly, the end range of motion improving device 100 includes a frame 102, a first link member 104, a second link member 106, one or more actuators 108, a controller module 110, and a controller 112. More particularly, the first link member 104 is configured for being secured to an upper leg of a patient and configured for rotating the upper leg of the patient about a hip axis of the patient through a predetermined upper leg range of motion, the second link member 106 is configured for being secured to a lower leg of the patient and for rotating the lower leg of the patient about a knee axis of the patient through a predetermined lower leg range of motion. Further, the one or more actuators 108 are configured to rotate the first link member 104 about the hip axis and to rotate the second link member 106 about the knee axis. The first link member 104 and the second link member 106 are configured to rotate independently of one another. However, in certain embodiments, the first link member 104 and the second link member 106 may rotate concurrently. "Link member" as used herein may also be described as a "leg assembly".

Figure 2:
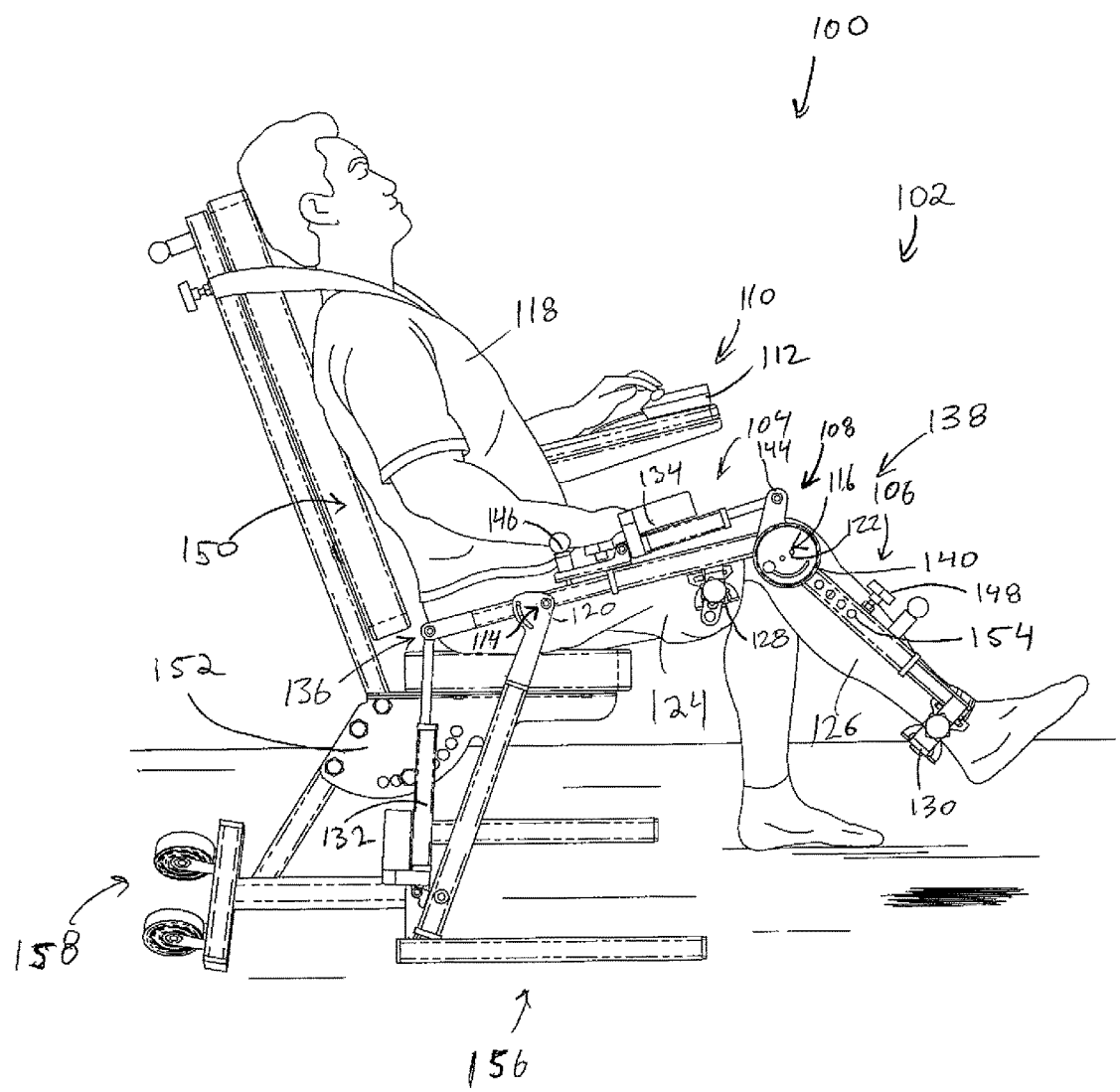
FIG. 2 is a side view of a patient using the end range of motion improving device.
Figure 3:
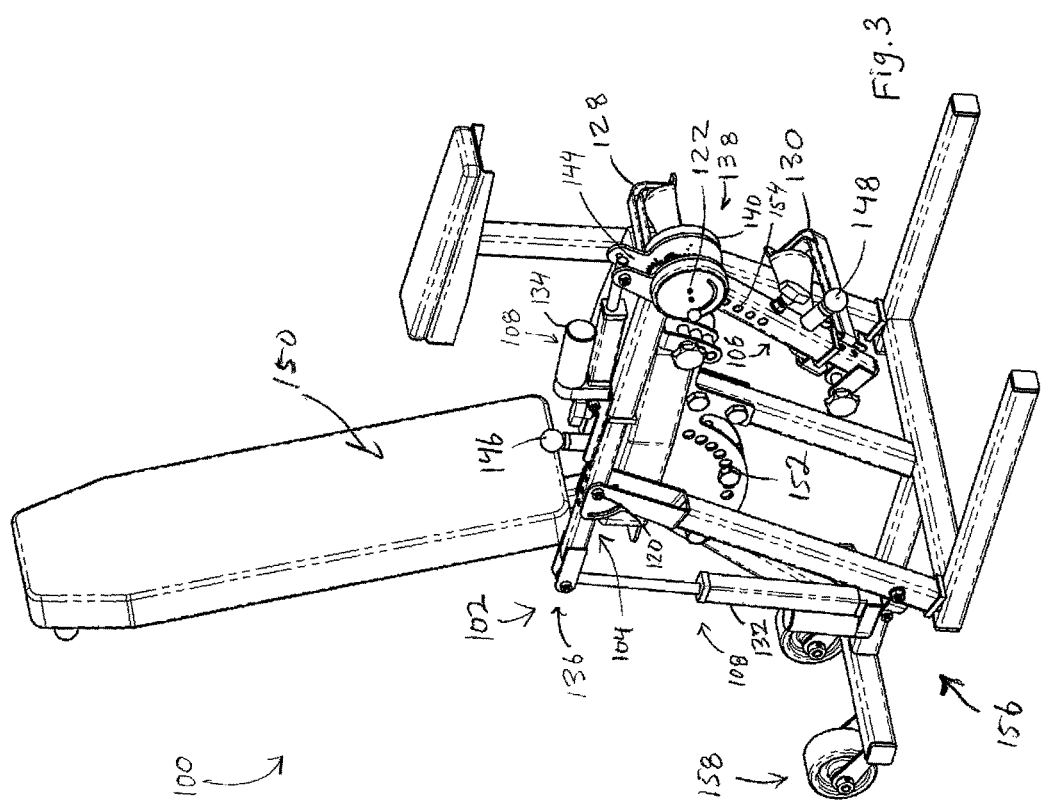
FIG. 3 is an isometric front view of the end range of motion improving device.

For example, FIG. 2 shows the end range of motion improving device 100 being used by a patient. More particularly, FIG. 2 shows a hip axis 114 of the patient anatomically aligning with a first link member axis 120, and a knee axis 116 of the patient anatomically aligning with a second link member axis 122. The hip axis 114 and the knee axis 116 are generally coaxial or parallel, and the first link member axis 120 and the second link member axis 122 are substantially coaxial or parallel. The first link member is secured to the upper leg 124 via an upper leg securing mechanism 128, and the second link member is secured to the lower leg 126 via a lower leg securing mechanism 130. For example, the upper leg securing mechanism 128 and the lower leg securing mechanism may support the upper leg 124 and the lower leg 126 respectively such that when the first link member 104 and the second link member 106 rotate, respectively, the upper leg 124 rotates about the patient hip axis 114 and/or the lower leg 126 rotates about the knee axis 116 of the patient 118. For example, the upper leg securing mechanism 128 and the lower leg securing mechanism 130 may include various pads and straps to secure limbs of the patient. Further, the upper leg securing mechanism 128 and the lower leg securing mechanism 130 may include various adjustment means to adjust height or width to provide comfort to a patient and to anatomically match the various rotational axes as described herein. More particularly, the upper leg securing mechanism 128 and the lower leg securing mechanism 130 may include a concave pad with a semi-spherical cross section. The lower leg securing mechanism 130 may include a footplate that includes adjusting means to a control, guide or limit plantar and dorsiflexion of the ankle. Further, upper leg securing mechanism and lower leg securing mechanism may be configured to limit knee varus or valgus rotation when the upper leg 124 or lower leg 126 is rotated.

The one or more actuators 108 may be configured in various ways to actuate and rotate the first link member 104 and the second link member 106. For example, the one or more actuators 108 may be linear actuators of various appropriate stroke lengths. For example, the one or more actuators 108 may be Geming® brand 4" or 8" industrial linear actuators. To rotate the link members, the one or more actuators 108 and the link members may be connected or attached in various ways. For example the first link member 104 may be pivotably attached to the frame 102 to form the first link member axis 120. First actuator 132 may be pivotably attached to the frame and to first end 136 of the first link member such that the first link member 104 may pivot about the first link member axis 120 when the first actuator 132 lengthens or shortens.

Figure 4:
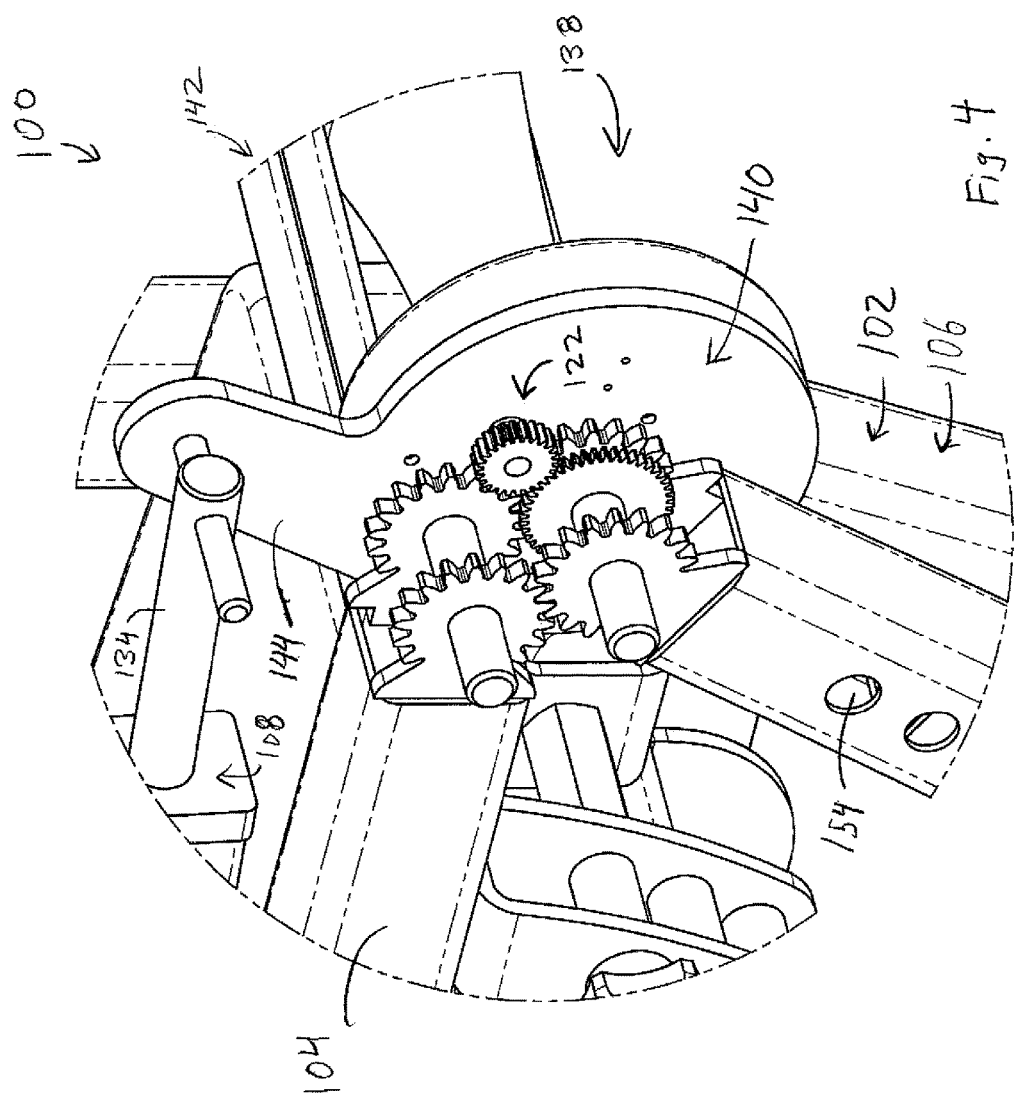
FIG. 4 is a perspective enlarged view of a gear system of the end range of motion improving device.

The second link member 106 may be pivotably attached or linked to a second end 138 of the first link member 104 that is opposite the first end 136. The second link member 106 may be linked to the first link member 104 via a member link 140. Member link 140 may include a hinge plate, or various housing elements. The member link 140 may be a gear system, or a hinge system, for example. Member link 140 is shown in FIG. 4 having a gear system 142. Particularly, gear system 142 may include various polycentric and/or non-polycentric gears to imitate or provide anatomical rotation similar to that of a human knee. For example, an appropriate polycentric gear system 142 may include planetary gears positioned adjacent to or meshed with a set of sun gears when the second actuator 134 causes the member link 140 to rotate via applying linear force to appendage 144, where appendage 144 acts as a lever. Any appropriate number of teeth may be included in the various gears in the gear system 142. For example, less teeth may produce a greater degree of travel for any one of the gears, with less actuator motion. For example, the planetary gears and the sun gears may have a same number of teeth. One or more potentiometers may be included in gear system 142 such that voltage readings may be obtained for gear rotation angles, and such voltage readings may be recorded as usage data. Including gears with more teeth may provide finer voltage sensing. Gear system 142 and one or more actuators 108 may include any appropriate force and/or angle sensors that output sensor data to control module 110 for processing. Further, such force and/or angle sensors may be included in the upper leg securing mechanism or the lower leg securing mechanism. For example, force and/or angle sensors may be included in a pad that engages a user's leg. Turning back to FIG. 2, a second actuator 134 may be pivotably attached to the first link member 104 and the second link member 106 such that when the second actuator lengthens or shortens, the second link member rotates about the second link member axis 122. The second link member axis 122 may be formed by member link 140 or by any appropriate rotational linkage means at second end 138. For example, member link 140 may include an appendage 144 where the second actuator 134 may be pivotably attached such that the member link 140 acts as a lever to rotate the second link member 106 when the appendage 144 is rotated via the lengthening or shortening of the second actuator 134. Appendage 144 take form as a lever arm or a lever.

Figure 5:
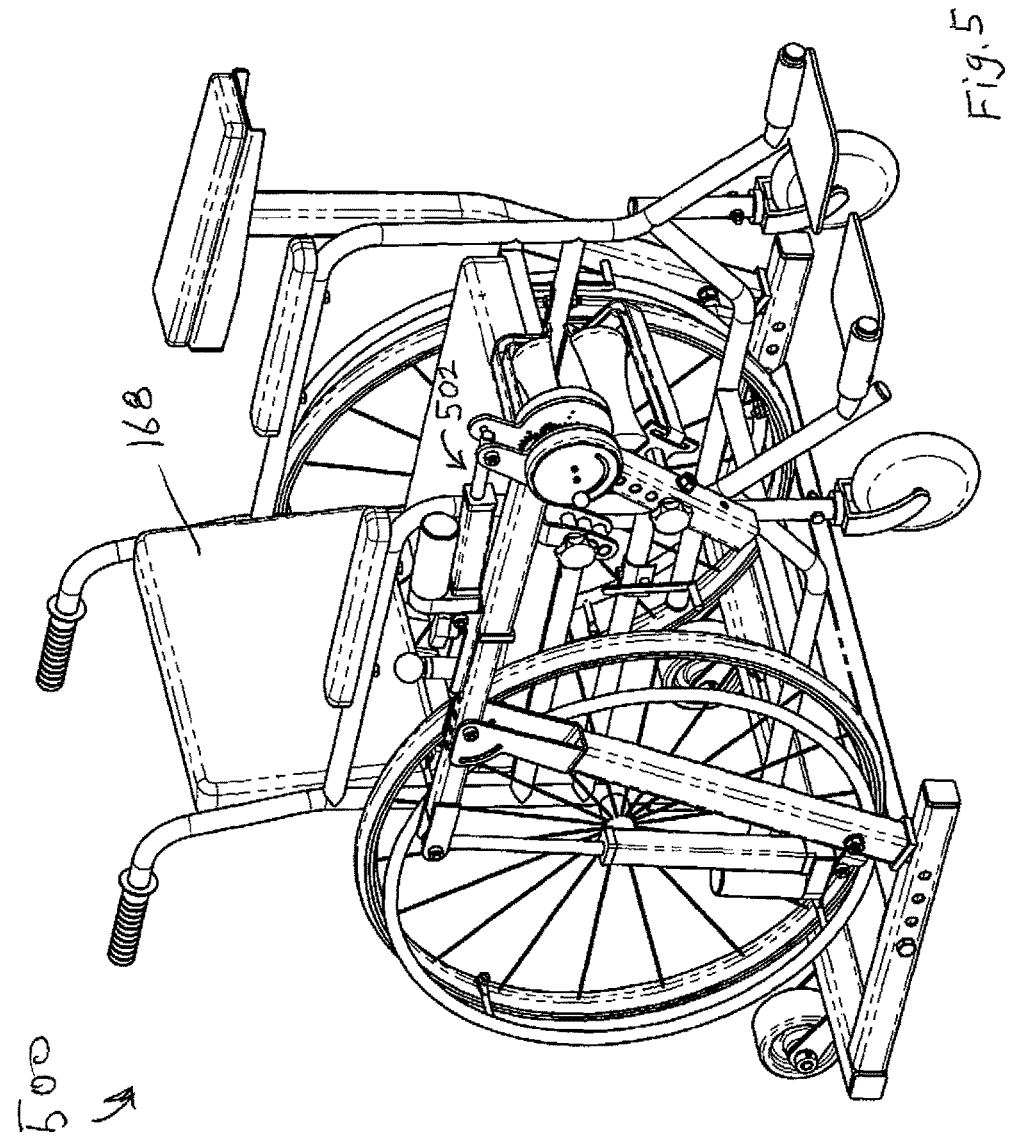
FIG. 5 is an isometric front view of another embodiment of end range of motion improving device where the end range of motion improving device is attached to a wheelchair.

The end range of motion improving device 100 includes various adjustment or comfort means to anatomically match the first link member axis 120 and the second link member axis 122 with patient hip axis 114 and knee axis 116, respectively. For example, first link member 104 may include a first adjustment means 146 to elongate or shorten the first link member 104 to adjust and anatomically match the first link member axis 120 with the hip axis 114, and the second link member axis 122 with the knee axis. For example, the first link member may include a telescoping shaft with various holes that a plunger may engage to selectively secure an effective length of the first link member. Similarly, the second link member may include a second adjustment means 148 to adjust to a tibial length or a lower leg 126 length such that the knee axis 116 anatomically matches the second link member axis 122 when a patient's leg is strapped or secured to the second link member 106. Further, a seat 150 may be attached to the frame 102 such that the seat 150 may be adjusted for patient comfort or most importantly to anatomically match the hip axis 114 and the knee axis 116 with the first link member axis 120 and the second link member axis 122. For example, seat 150 may include a seat adjustment means 152 to change a seat-to-backrest angle so that a patient's hip-to-lower leg angle may be adjusted. Further in another embodiment, an end range of motion improving device 500 may include means to attach a wheelchair 168 to frame 502 as a seat shown in FIG. 5. End range of motion improving device 500 appropriately includes all features of end range of motion improving device 100. Further, for amputee support, various modifications may be made to second link member 106 such as to adjust and attach the lower leg securing mechanism 130 to holes 154 such that a below-knee amputee patient may secure rotate their lower leg using the disclosed device.

Base 156 may take any appropriate form to provide stability and support for frame 102 and patient 118. Further, base 156 may include wheels 158 such that the frame 102 may be conveniently transported across a surface on which the frame 102 rests. Further, frame 102 may include various arm rests to provide comfort, or to provide a surface for controller 112 to be conveniently placed. It is to be understood that frame 102 may be assembled to provide therapy to any leg of a patient.

Figure 12:
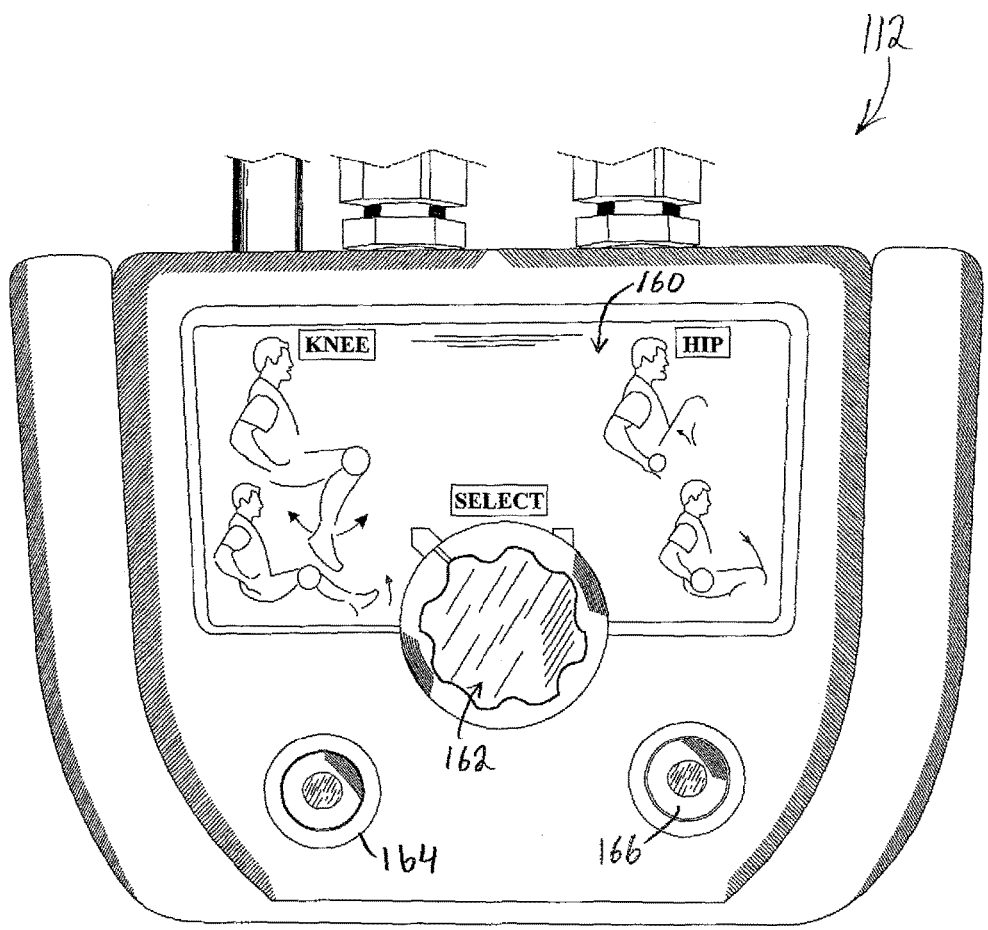
FIG. 12 shows a controller of the end range of motion improving device.

The one or more actuators may be driven to rotate respective limbs of a patient in response to a manual or automatic controller or control module input. For example, the controller 112 is shown in FIG. 2 receiving a user input. FIG. 12 shows controller 112 in more detail. For example, controller 112 includes a display 160 that displays various usage data, parameters, instructions or indicators relating to usage of the end range of motion improving device 100. For example, usage data may include time using the end range of motion improving device 100, sensed force data applied from or to the limbs of a patient, maximum and minimum angles reached via flexion, extension or hip rotation, time a patient holds a particular angle such as a maximum or minimum angle, and/or number of cycles completed of a particular therapy exercise. Further, controller 112 includes various user input means. For example, controller 112 may include a touch screen LCD display to provide user input, or may include various tactile, physical, and mechanical buttons. As a non-limiting example, controller 112 includes a selector 162. Selector 162 is configured such that the patient 118 or a user is able to select whether they want to rotate their upper leg 124 or their lower leg 126 while secured to the end range of motion improving device 100. First button 164 and second button 166 may be used to rotate the selected leg portion (i.e. upper leg or lower leg) via extension or flexion respectively, or as indicated by display 160 of controller 112. For example, the patient 118 may select "knee" then choose to rotate their lower leg about the knee axis 116. Likewise, the patient 118 may select "hip" then choose to rotate their upper leg about the hip axis 114. The controller 112 is wired and configured such that patient 118 may choose to rotate their upper leg 124 or lower leg 126 independently. Alternatively, controller 112 may act as a means to allow a user or patient 118 to rotate both the upper leg 124 and the lower leg 126 concurrently in any desired rotation direction (i.e. flexion or extension). The controller 112 allows a user to rotate the respective limbs by sending a signal via controller module 110 to rotate first link member 104 and/or second link member 106. It is to be understood that controller 112 may include variations in its user interface. For example, various joysticks or trackballs may be provided for a user to control rotation of their limbs as describe herein. In embodiments where a computer processor is included in controller module 110, the computer processor may include a storage machine holding instructions executable by a logic machine, the instructions being any appropriate computer readable instruction indicated, mentioned or described herein.

Controller module 110 includes means to provide controller 112 with readout information about the end range of motion improving device 100. For example, the end range of motion device 100 may include various sensors that provides the controller module and subsequently the controller with information such as force data related to forces applied to a patient's limb or forces applied to the first link member 104 or the second link member 106 or the first link member axis 120 or the second link member axis 122. Further, the controller may be provided with sensor information relating to angle. For example, the controller may display angle readout information for current angles of first link member 104 and the second link member 106. Further, controller module 110 may include means to connect controller module 110 to a network such that the controller module 110 may receive computer instructions from the network, may be controlled remotely via a remote device, or may upload or send usage report data to a server on the network for further processing. For example, controller module 110 may be connected to a computer network such that the controller module 110 and controller 112 may be shut down, controlled, or rotation parameters may be adjusted or inputted. Further, a current location of the end range of motion improving device 100 may be determined or uploaded via the computer network. For example, controller module 110 may receive input control signals or parameters locally or remotely to automatically cycle rotating first link member 104 or second link member 106 through predetermined rotation limits, or predetermined force limits. The controller module 110 may be set to automatically cycle between a range of motion while holding a particular angle for a particular time at various angle increments, while remaining within a certain force threshold. Controller module 110 may be indicated to stop automatically rotating when the controller module 110 is supplied with sensor inputs that pass a predetermined force or rotation threshold. As such, force sensors or rotation sensors may be included to provide force and rotation usage information. Therefore, controller module 110 or end range of motion improving device 100 may include various appropriate computer processors or computer components to provide such features. For example end range of motion improving device 100 may include various wireless or Bluetooth devices to wirelessly connect controller 112, controller module 110 or any appropriate component to a computer network to provide the functions described herein. Further, controller 112 or controller module 112 may include more than one controller, such as a slave controller hard wired to the end range of motion improving device 100 or a wireless pendant that controls the slave controller or control module 110, the pendant being conveniently locatable in a user's hand. Additionally, controller module 110 or controller 112 may include an "abort" button that disengages rotation if a patient experiences extreme discomfort or injury, or if the end range of motion improving device 100 malfunctions. For example, such an "abort" button may be a user input to send signals to controller module 112 to reverse forces applied to the patient's upper leg or lower leg.

Force and/or angle data may be processed by the end range of motion device 100 to provide various exercise modes to a patient. For example, a patient may be prescribed to engage in isometric exercises. To apply isometric exercise, a patient may be indicated by display 160 or by a physical therapist to apply force via their lower leg or upper leg to the first link member 104 or second link member 106. As such, sensing forced applied by a patient may be used to determine patient strength, or progress.

Further, a patient may be indicated by a health professional to engage in contract relax therapy, where a patient presses against the first link member or the second link member in an opposite direction of link member rotation such that the patient's muscles and tendons increase range of motion and a "stretch reflex" is minimized. For example, during stretching, a leg muscle (e.g. a hamstring) may reflexively apply a force in response to an opposing force. Such contract relax therapy may reduce such a "stretch reflex", and sensing forces and angles via the various sensors disclosed herein provides this functionality.

Even further, eccentric or concentric exercise may be prescribed to a patient, and such exercises are enabled by the end range of motion device 100 via the force and angle sensors described herein. For example, eccentric exercise may include a patient pressing against the second link member while simultaneously rotating the second link member in an opposite direction to the applied force. On the other hand, concentric exercise may include a patient applying a force to the second link member while rotating the second link member in a same direction of the applied force.

Figure 6:
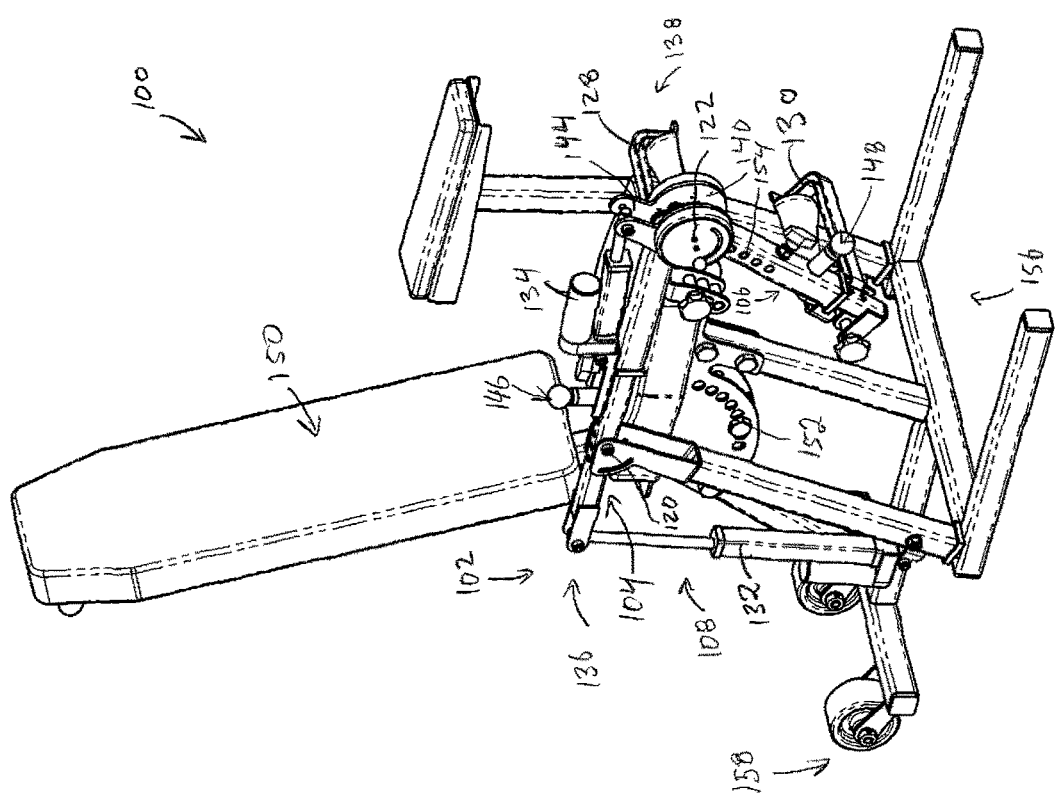
FIG. 6 is an isometric front view of the end range of motion improving device in a first position.
Figure 7:
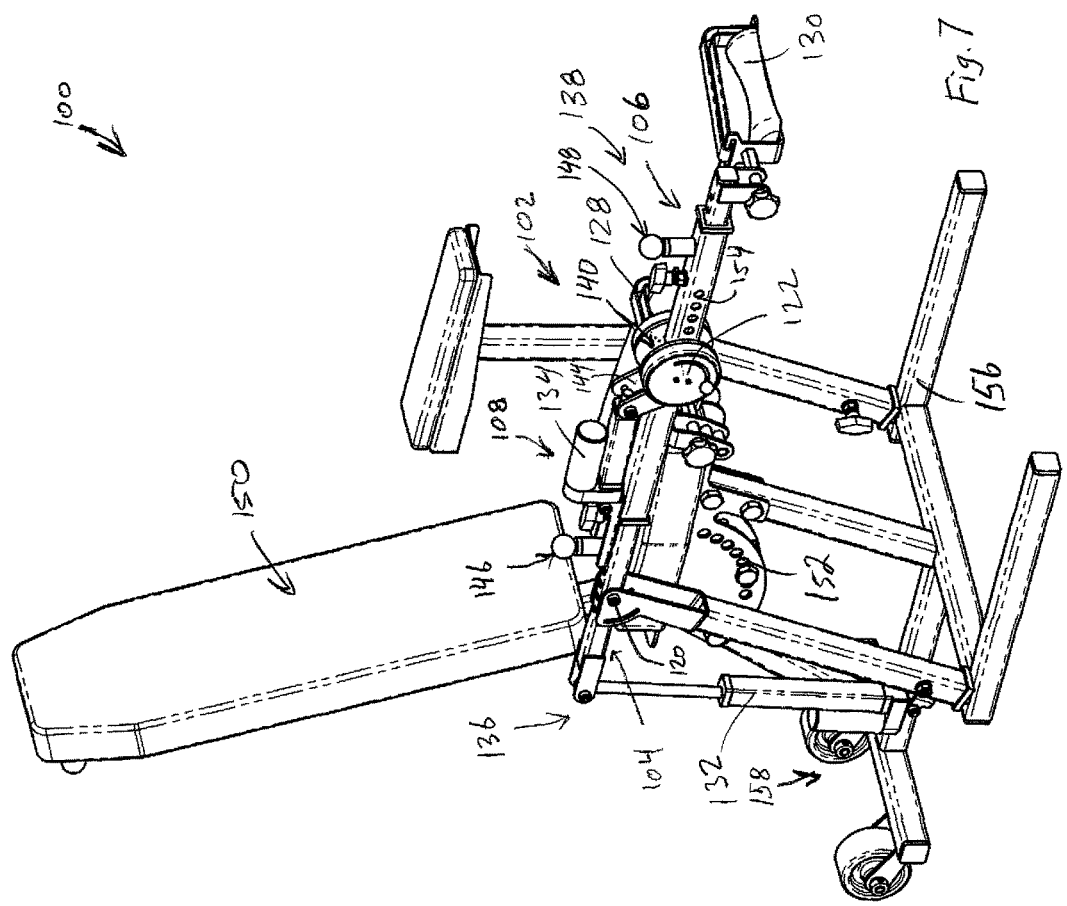
FIG. 7 is an isometric front view of the end range of motion improving device in a second position.
Figure 8:
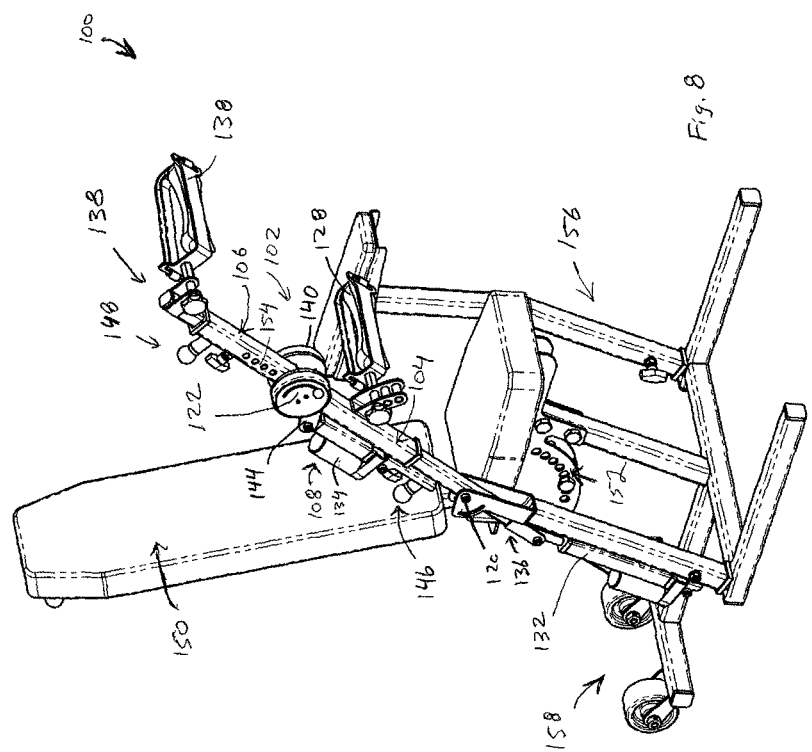
FIG. 8 is an isometric front view of the end range of motion improving device in a third position.
Figure 9:
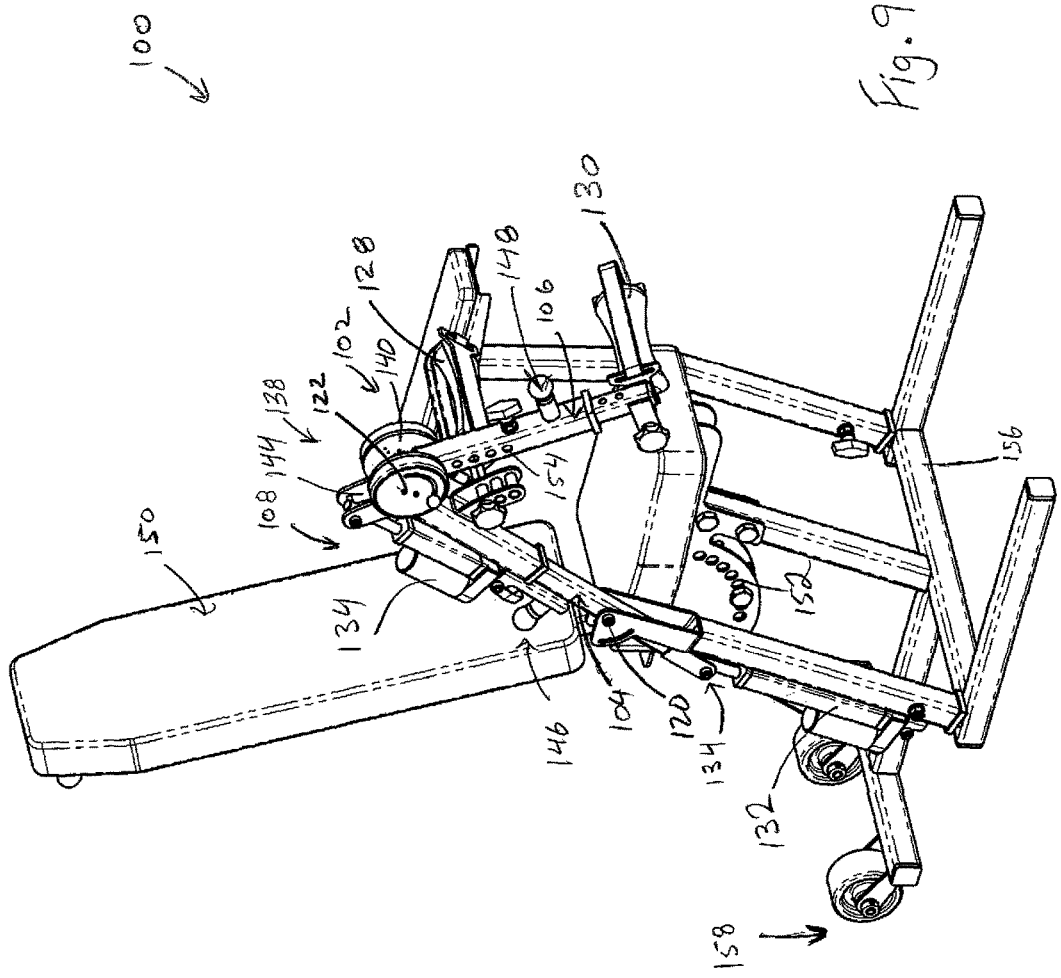
FIG. 9 is an isometric front view of the end range of motion improving device in a fourth position.
Figure 10:
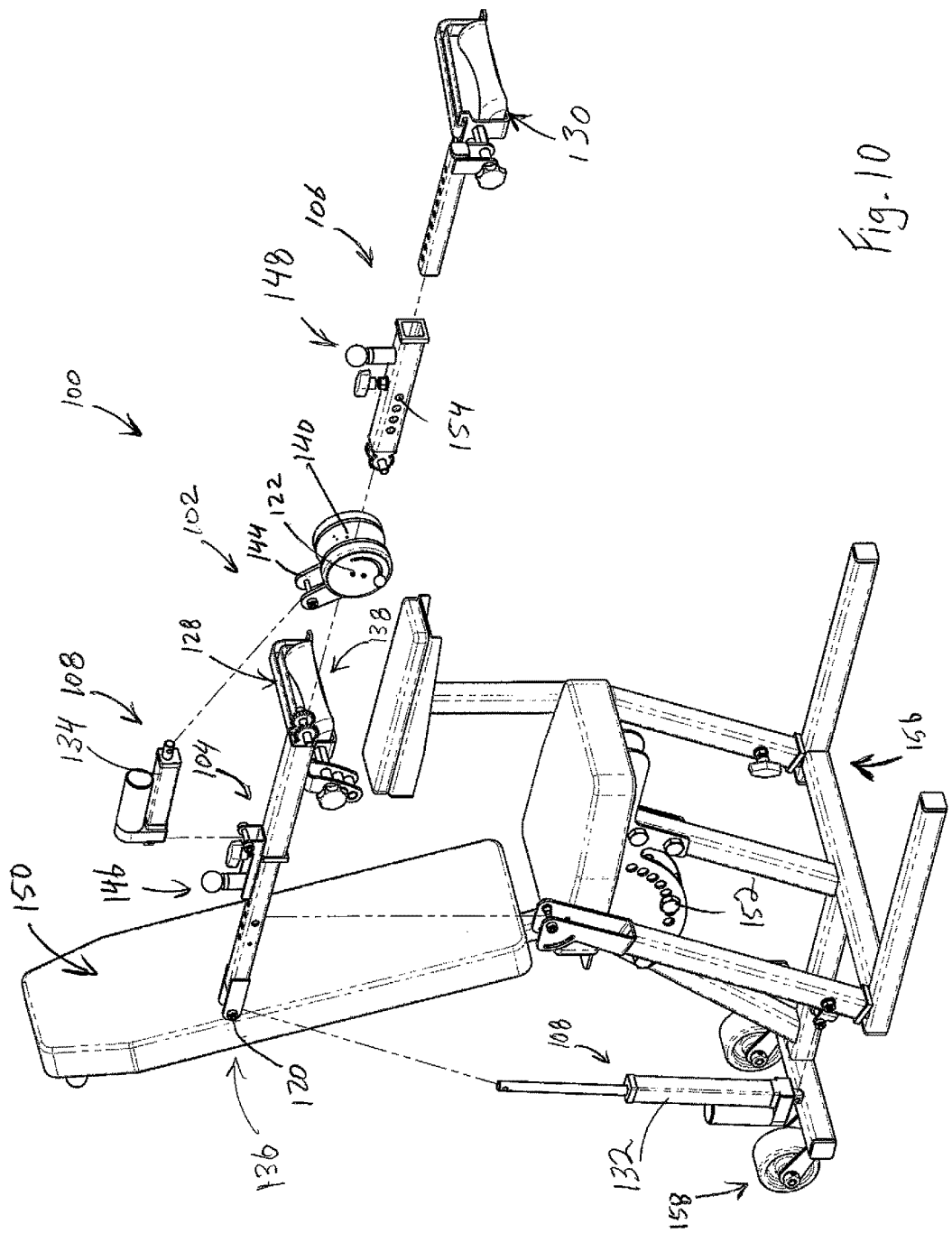
FIG. 10 is an isometric front exploded view of the end range of motion improving device.
Figure 11:
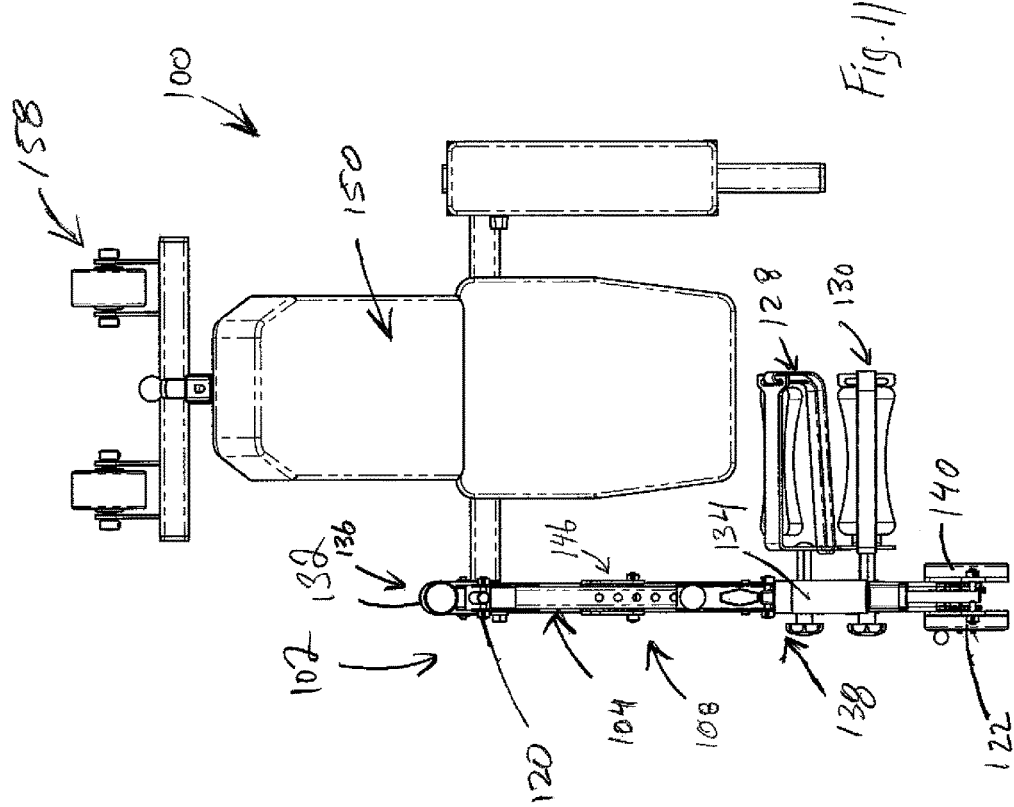
FIG. 11 is a plan view of the end range of motion improving device.

FIGS. 6-9 illustrate an exemplary sequence of positions of first link member 104 and second link member 106. Particularly FIG. 6 shows first link member 104 set at 0° and second link member 106 rotated to 135° flexion. FIG. 7 shows first link member 104 still set at 0° while second link member 106 has been rotated to 0° extension. FIG. 8 shows rotating or setting first link member 104 to −45° while maintaining or keeping second link member set at 0°. And lastly, FIG. 9 shows maintaining or keeping the first link member set at −45° as in FIG. 8, but rotating second link member back to a 45° angle. As such, the second link member and the first link member may rotate independent of each other. For example, a patient's upper leg may be brought to the −45° angle of FIG. 8 to stretch hamstrings or various connective tissue of the hip joint.

Disclosed is an end range of motion improving device including a first link member configured for being secured to an upper leg of a patient and being rotatable about a first axis for rotating the upper leg of the patient about a hip axis of the patient through an upper leg range of motion. Further, the end range of motion improving device includes a second link member configured for being secured to a lower leg of the patient and being rotatable about a second axis for rotating the lower leg of the patient about a knee axis of the patient through a lower leg range of motion, said second axis being displaceable into a selectable fixed position and maintaining said fixed position during rotation of said second link member. The end range of motion improving device also may include one or more actuators for rotating the second link member about the second link axis. The frame includes an attachment means to attach a seat. The second link member may include a lower leg support to rotate the lower leg of the patient about the knee axis. The first link member rotates about a first axis provided by a first axis assembly to rotate the upper leg and the second link member rotates about a second axis provided by a second axis assembly to rotate the lower leg.

The disclosed controller is configured for controlling the at least one actuator for selectively rotating the first link member about the hip axis through the upper leg range of motion and selectively rotating the second link member the knee axis through the lower leg range of motion.

However, it is to be understood that the end range of motion improving device may instead include only the disclosed second link member, or only the disclosed first link member without departing from scope of this disclosure. Further, the first link member or the second link member does not have to be rotatable. For example, the first link member may be a stand or a simple support that does not rotate and supports or facilitates the rotation of the second link member. This configuration is a simpler machine, and may be easier to provide in a person's home.

In some embodiments, the first link member is configured for being secured to an upper leg of a patient and is rotatable about a first link member axis for rotating the upper leg of the patient about a hip axis of the patient through an upper leg range of motion. The first link member may include an upper leg support for supporting the upper leg on the first link member. the second link member includes a lower leg support for supporting the lower leg on the second link member. The second link member includes a lower leg support to rotate the lower leg of the patient about the knee axis. The first link member rotates about a first axis provided by a first axis assembly to rotate the upper leg and the second link member rotates about a second axis provided by a second axis assembly to rotate the lower leg. At least one of the first axis assembly and the second axis assembly includes a hinge system. At least one of the first axis assembly and the second axis assembly includes a gear system. The second axis assembly links the first link member to the second link member. The first axis assembly links a base of the frame to the first link member. The first link member independently rotates about the first axis without causing the second link member to rotate about the second axis, and the second link member independently rotates about the second axis without causing the first link member to rotate about the first axis. The first link member independently rotates about the first axis without causing the second link member to rotate about the second axis, and the second link member independently rotates about the second axis without causing the first link member to rotate about the first axis. The frame may include one or more adjustment means to anatomically match the first axis to the hip axis and the second axis to the knee axis. The base may include wheels to wheel the frame across a surface on which the base rests. The gear system includes a polycentric gear system. The controller module registers usage data. The usage data includes time that at least one of the first and second link members have spent at a particular angle. The usage data includes a current angle of at least one of the first and second link members. The usage data includes a maximum and minimum angle reached by at least one of the first and second link members. The usage data includes force data from forces applied to at least one of the first and second link members. The controller sets rotation limits for at least one of the first link member and second link member. The controller sets force limits for at least one of the first link member and second link member. The controller is set to shut down after a predetermined shut down time via user input. The controller is set to hold for a predetermined pause time at least one of the upper leg and second link member at an angle at which either the rotation limit or the force limit is registered by the control module. The controller may be set to cause at least one of the first link member and second link member to automatically rotatably cycle between at least one of the force limit and rotation limits for a predetermined number of cycles, and the control module registers the number of cycles executed. The usage data may include the number of cycles executed. The controller is set to automatically rotatably cycle the upper and/or second link member between at least one of limits in increments of rotation while holding an angle at each increment for a predetermined increment pause time set by the control module. The control module includes a display configured to read out one or more of the usage data, force limit, rotation limits, shut down time, pause time, predetermined number of cycles, executed number of cycles, and increment pause time. The usage data, force limit, rotation limits, shut down time, pause time, predetermined number of cycles, executed number of cycles, and increment pause time is reported to a server via a computer network. The controller is controllable via a remote device through a computer network.

In some embodiments, the end range of motion improving and reporting system may include one or more storage machines holding instructions executable by one or more logic machines to receive a set of parameters, execute an automated cycle based on the parameters to automatically rotate at least one of an upper leg of a patient about a hip axis of the patient and a lower leg of the patient about a knee axis of the patient, record report data, and send the report data to a remote database. The set of parameters includes a maximum angle and a minimum angle. The set of parameters includes a maximum force applied to at least one of the upper leg and lower leg. The set of parameters includes time that at least one of the first and second link members is to spend at a particular angle. The instructions are executable to receive usage data, the usage data including at least one of a current angle of the upper leg and the lower leg, a force value, number of executed cycles, and total running time. The instructions are executable to rotate the upper leg independently about the hip axis without causing the lower leg to rotate about the knee axis, or to independently rotate the lower leg about the knee axis without causing the first link member to rotate about the hip axis. The instructions include to display at least one of the usage data and the set of parameters. The instructions are executable to receive instructions from a remote device via a computer network.

Disclosed is also a method of providing end range of motion therapy, the method comprising the following steps. For example, the following steps may be carried out or executed via a computing system that includes a processor, memory, storage machine, a communications subsystem, and display subsystem. The method includes providing the end range of motion improving device, providing a user input to the controller for rotating the second link member, providing a user input to the controller for indicating therapy, parameters, and rotating the lower leg according to the user input and the therapy parameters. configuring the first link member to be secured to an upper leg of a patient and to be rotatable about a first link member axis for rotating the upper leg of the patient about a hip axis of the patient through an upper leg range of motion; providing a user input to the controller for rotating the first link member; and rotating the upper leg according to the user input and the therapy parameters.

A method of providing end range of motion therapy may also include receiving usage data, generating report data based on the usage data, sending the report data to a server, and processing the report data on the server, preparing the end range of motion improving device prior to the providing step by adjusting at least one of a first link member length, a second link member length, and therapy parameters. The parameters may include at least one of a maximum angle and a minimum angle, a maximum force applied, time to spend at a particular angle, and number of rotational cycles. The usage data may include at least one of a current angle of the upper leg and the lower leg, a force value, number of executed cycles, and total running time. Rotating at least one of the upper leg and the lower leg includes independently rotating the first link member about the hip axis without rotating the second link member about the knee axis or independently rotating the second link member about the knee axis without rotating the first link member about the hip axis. The method may include, displaying at least one of the usage data and the set of parameters. Receiving a user input includes receiving input from a remote device via a network. Receiving the user input includes shutting down the end range of motion improving device. Receiving the user input includes resetting the end range of motion improving device. The usage data may include a location of the end range of motion improving device.

We claim:

1. An end range of motion improving device comprising:
    a linkage, the linkage including:
    a first link member;
    a second link member supported on the first link member, the second link member configured for being secured to a lower leg of a patient and being rotatable about a second link member axis for rotating the lower leg of the patient about a knee axis of the patient through a lower leg range of motion, the second link member axis being displaceable into a selectable fixed position aligned with the knee axis and maintaining the fixed position during rotation of the second link member;
    an actuator for rotating the second link member about the second link member axis; and
    a controller controlling the actuator for selectively rotating the second member link member about the second link axis through the lower leg range of motion.

2. The end range of motion improving device according to claim 1, wherein the first link member is configured for being secured to an upper leg of the patient and is rotatable about a first link member axis for rotating the upper leg of the patient about a hip axis of the patient through an upper leg range of motion.

3. The end range of motion improving device according to claim 2, wherein the second link member includes a lower leg support to rotate the lower leg of the patient about the knee axis.

4. The end range of motion improving device according to claim 1, wherein the second link member includes a lower leg support for supporting the lower leg on the second link member.

5. A method of providing end range of motion therapy, the method comprising:
    providing the end range of motion improving device according to claim 1,
    providing a user input to the controller for rotating the second link member;
    providing a user input to the controller for indicating therapy parameters; and
    rotating the lower leg according to the user input and the therapy parameters.

6. The method according to claim 5, further comprising:
    configuring the first link member to be secured to an upper leg of the patient and to be rotatable about a first link member axis for rotating the upper leg of the patient about a hip axis of the patient through an upper leg range of motion;
    providing a user input to the controller for rotating the first link member; and
    rotating the upper leg according to the user input and the therapy parameters.

7. An end range of motion improving device comprising:
    a linkage, the linkage including:
    a first link member;
    a second link member mounted on the first link member, the second link member configured for being secured to a lower leg of a patient and being rotatable about a second link member axis for rotating the lower leg of the patient about a knee axis of the patient through a preset lower leg range of motion, the second link member axis being displaceable into a selectable fixed position aligned with the knee axis by an adjustment of the first link member, the fixed position being maintained during rotation of the second link member;

an actuator for rotating the second link member about the second link member axis; and a controller controlling the actuator for selectively rotating the second link member about the second link member axis through the preset lower leg range of motion.

\* \* \* \* \*

(12) EX PARTE REEXAMINATION CERTIFICATE (11810th)
United States Patent
Marti et al.

(10) Number: US 9,873,010 C1
(45) Certificate Issued: *Mar. 2, 2021

(54) RANGE OF MOTION IMPROVEMENT DEVICE

(71) Applicants: Eduardo M. Marti, Sunrise, FL (US); Robert T. Kaiser, South Hampton, NJ (US)

(72) Inventors: Eduardo M. Marti, Sunrise, FL (US); Robert T. Kaiser, South Hampton, NJ (US)

(73) Assignee: T-REX INVESTMENT, INC., Mount Pleasant, SC (US)

Reexamination Request:
No. 90/014,518, May 27, 2020

Reexamination Certificate for:
Patent No.: 9,873,010
Issued: Jan. 23, 2018
Appl. No.: 15/612,541
Filed: Jun. 2, 2017

(*) Notice: This patent is subject to a terminal disclaimer.

Related U.S. Application Data

(63) Continuation of application No. 14/730,574, filed on Jun. 4, 2015, now Pat. No. 9,669,249.
(Continued)

(51) Int. Cl.
*A63B 21/00* (2006.01)
*A61B 5/11* (2006.01)
(Continued)

(52) U.S. Cl.
CPC ...... *A63B 21/00069* (2013.01); *A61B 5/1114* (2013.01); *A61B 5/1121* (2013.01); *A61B 5/4585* (2013.01); *A61B 5/6828* (2013.01); *A61B 5/6835* (2013.01); *A61H 1/024* (2013.01); *A61H 1/0244* (2013.01); *A63B 21/00178* (2013.01); *A63B 21/00181* (2013.01); *A63B 21/4011* (2015.10); *A63B 21/4031* (2015.10); *A63B 23/0405* (2013.01); *A63B 23/0482* (2013.01); *A63B 23/0494* (2013.01); *A63B 24/0087* (2013.01); *A63B 71/0622* (2013.01); *G05G 9/047* (2013.01); *A61B 5/22* (2013.01); *A61B 5/6831* (2013.01); *A61B 5/6894* (2013.01); *A61B 5/6895* (2013.01); *A61B 2505/09* (2013.01); *A61H 2201/0149* (2013.01); *A61H 2201/0176* (2013.01); *A61H 2201/0192* (2013.01); *A61H 2201/1215* (2013.01); *A61H 2201/1642* (2013.01); *A61H 2201/1676* (2013.01); *A61H 2201/501* (2013.01); *A61H 2201/5043* (2013.01); *A61H 2201/5061* (2013.01); *A61H 2201/5069* (2013.01); *A61H 2201/5076* (2013.01); *A61H 2201/5097* (2013.01); *A61H 2203/0431* (2013.01); *A61H 2205/102* (2013.01); *A63B 21/0023* (2013.01); *A63B 21/4047* (2015.10); *A63B 23/03508* (2013.01); *A63B 2023/006* (2013.01); *A63B 2024/0068* (2013.01); *A63B 2071/0018* (2013.01); *A63B 2071/0081* (2013.01); *A63B 2071/065* (2013.01); *A63B 2071/0647* (2013.01); *A63B 2208/0233* (2013.01);
(Continued)

(58) Field of Classification Search
None
See application file for complete search history.

(56) References Cited

To view the complete listing of prior art documents cited during the proceeding for Reexamination Control Number 90/014,518, please refer to the USPTO's public Patent Application Information Retrieval (PAIR) system under the Display References tab.

*Primary Examiner* — Terrence R Till

(57) ABSTRACT

An end range of motion improving device is disclosed including, first and second link members to independently rotate an upper leg and a lower leg of a patient, having a controller to selectively rotate the link members, and a networked computing system to facilitate communication between the controller and other networked devices.

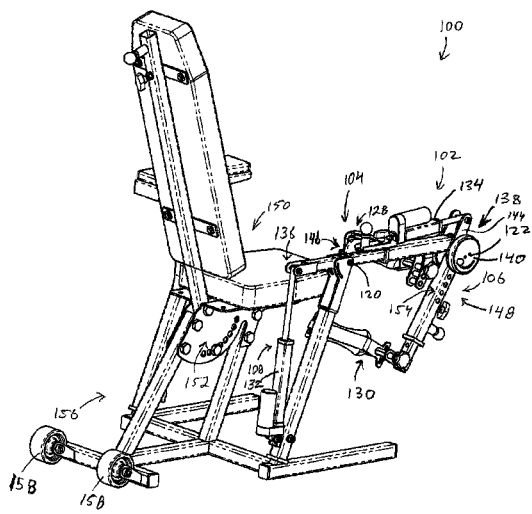

Related U.S. Application Data

(60) Provisional application No. 62/134,633, filed on Mar. 18, 2015, provisional application No. 62/042,399, filed on Aug. 27, 2014, provisional application No. 62/007,541, filed on Jun. 4, 2014.

(51) Int. Cl.
*A61B 5/00* (2006.01)
*A61H 1/02* (2006.01)
*A63B 23/04* (2006.01)
*A63B 24/00* (2006.01)
*A63B 71/06* (2006.01)
*G05G 9/047* (2006.01)
*A61B 5/22* (2006.01)
*A63B 21/002* (2006.01)
*A63B 23/035* (2006.01)
*A63B 23/00* (2006.01)
*A63B 71/00* (2006.01)

(52) U.S. Cl.
CPC ....... *A63B 2220/16* (2013.01); *A63B 2220/17* (2013.01); *A63B 2220/51* (2013.01); *A63B 2225/093* (2013.01); *A63B 2225/50* (2013.01); *G08C 2201/42* (2013.01)

US 9,873,010 C1

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-6 are cancelled.

Claim 7 is determined to be patentable as amended.

New claims 8-59 are added and determined to be patentable.

7. An end range of motion improving [device] *system* comprising:
   a linkage, the linkage including:
   a first link member *configured to be secured to an upper leg of a patient and that is rotatable about a first link member axis to rotate the upper leg of the patient about a hip axis of the patient through an upper leg range of motion*;
   a second link member mounted on the first link member, the second link member configured for being secured to a lower leg of [a] *the* patient and being rotatable about a second link member axis for rotating the lower leg of the patient about a knee axis of the patient through a preset lower leg range of motion, the second link member axis being displaceable into a selectable fixed position aligned with the knee axis by an adjustment of the first link member, the fixed position being maintained during rotation of the second link member;
   an actuator for rotating the second link member about the second link member axis; and
   a controller controlling the actuator for selectively rotating the second link member about the second link member axis through the preset lower leg range of motion[,]*;*
   *wherein the preset lower leg range of motion about the knee axis of the patient is between about 0 degrees extension and about 135 degrees flexion; and*
   *wherein the first link member independently rotates about the first link member axis without causing the second link member to rotate about the second link member axis, and the second link member independently rotates about the second link member axis without causing the first link member to rotate about the first link member axis.*

8. *The end range of motion improving system according to claim 7, wherein the first link member includes an upper leg support.*

9. *The end range of motion improving system according to claim 7, wherein the second link member includes a lower leg support.*

10. *The end range of motion improving system according to claim 7, wherein the controller registers, at least one of:*
    *(i) time that the second link member has spent at a particular position, or*
    *(ii) force data from forces applied to the second link member.*

11. *The end range of motion improving system according to claim 7, wherein the controller is configured to, at least one of:*
    *(i) automatically hold the second link member at a particular position for a predetermined pause time,*
    *(ii) automatically and rotationally cycle the second link member between a first position and a second position, or*
    *(iii) automatically and rotationally cycle the first link member between a first position and a second position.*

12. *The end range of motion improving system according to claim 7, wherein the linkage further comprises one or more adjustable mechanisms to anatomically match the first link member axis to the hip axis of the patient.*

13. *The end range of motion improving system according to claim 7, further comprising one or more storage machines holding instructions executable by one or more logic machines configured for:*
    *(i) receiving a set of parameters;*
    *(ii) rotating the second link member based on the set of parameters;*
    *(iii) recording report data; and*
    *(iv) sending the report data to a database.*

14. *The end range of motion improving system according to claim 13, wherein the set of parameters includes, at least one of:*
    *(i) a maximum angle and a minimum angle,*
    *(ii) a maximum force, or*
    *(iii) time that the second link member is to hold a particular position.*

15. *The end range of motion improving system according to claim 13, wherein the instructions are executable to:*
    *(i) rotate the first link member independently about the first link member axis without causing the second link member to rotate about the second link member axis, or*
    *(ii) independently rotate the second link member about the second link member axis without causing the first link member to rotate about the first link member axis.*

16. *The end range of motion improving system according to claim 7, wherein the first link member is rotatable about the first link member axis within a preset upper leg range of motion between about −45 degrees and about 0 degrees.*

17. *The end range of motion improving system according to claim 7, further comprising a frame configured to rest on a surface during use by the patient and remain stationary during the patient's leg motion.*

18. *The end range of motion improving system according to claim 17, wherein a seat is attached to the frame.*

19. *The end range of motion improving system according to claim 7,*
    *wherein the second link member is pivotably linked to the first link member via a polycentric gear system, and*
    *wherein the actuator for rotating the second link member and the polycentric gear system are connected such that movement of the actuator for rotating the second link member causes rotation of the polycentric gear system to rotate the second link member about the second link member axis.*

20. *An end range of motion improving system comprising:*
    *a frame configured to rest on a surface during use by a patient and remain stationary during the patient's leg motion; and*
    *a linkage connected to the frame, the linkage including:*
    *a first link member;*
    *a second link member supported on the first link member, the second link member configured for being secured to a lower leg of the patient, the* second link member being rotatable about a second link member axis for rotating the lower leg of the patient about a knee axis of the patient through a lower leg range of motion, the second link member axis being displaceable into a selectable fixed position aligned with the knee axis and maintaining the fixed position during rotation of the second link member;
an actuator for rotating the second link member about the second link member axis; and
a controller controlling the actuator for selectively rotating the second member link member about the second link member axis through the lower leg range of motion;
wherein the second link member is independently rotatable about the second link member axis without causing the first link member to rotate about a first link member axis such that the patient's knee may be rotated without causing the patient's hip to rotate about a hip axis.

21. The end range of motion improving system according to claim 20, wherein the first link member includes an upper leg support.

22. The end range of motion improving system according to claim 20, wherein the second link member includes a lower leg support.

23. The end range of motion improving system according to claim 20, wherein the controller registers, at least one of:
(i) time that the second link member has spent at a particular position, or
(ii) force data from forces applied to the second link member.

24. The end range of motion improving system according to claim 20, wherein the controller is configured to, at least one of:
(i) automatically hold the second link member at a particular position for a predetermined pause time,
(ii) automatically and rotationally cycle the second link member between a first position and a second position, or
(iii) automatically and rotationally cycle the first link member between a first position and a second position.

25. The end range of motion improving system according to claim 20, wherein the linkage further comprises one or more adjustable mechanisms to anatomically match the first link member axis to the hip axis of the patient.

26. The end range of motion improving system according to claim 20, further comprising one or more storage machines holding instructions executable by one or more logic machines configured for:
(i) receiving a set of parameters;
(ii) rotating the second link member based on the set of parameters;
(iii) recording report data; and
(iv) sending the report data to a database.

27. The end range of motion improving system according to claim 26, wherein the set of parameters includes, at least one of:
(i) a maximum angle and a minimum angle,
(ii) a maximum force, or
(iii) time that the second link member is to hold a particular position.

28. The end range of motion improving system according to claim 26, wherein the instructions are executable to:
(i) rotate the first link member independently about the first link member axis without causing the second link member to rotate about the second link member axis, or
(ii) independently rotate the second link member about the second link member axis without causing the first link member to rotate about the first link member axis.

29. The end range of motion improving system according to claim 20, wherein the first link member is independently rotatable about the first link member axis without causing the second link member to rotate about the second link member axis.

30. The end range of motion improving system according to claim 20, wherein the second link member is rotatable about the second link member axis within a preset lower leg range of motion between about 0 degrees extension and about 135 degrees flexion.

31. The end range of motion improving system according to claim 20, wherein the first link member is rotatable about the first link member axis within a preset upper leg range of motion between about −45 degrees and about 0 degrees.

32. The end range of motion improving system according to claim 20, wherein a seat is attached to the frame.

33. The end range of motion improving system according to claim 20,
wherein the second link member is pivotably linked to the first link member via a polycentric gear system, and
wherein the actuator for rotating the second link member and the polycentric gear system are connected such that movement of the actuator for rotating the second link member causes rotation of the polycentric gear system to rotate the second link member about the second link member axis.

34. An end range of motion improving system comprising:
a frame configured to rest on a surface during use by a patient and remain stationary during the patient's leg motion, wherein a seat is attached to the frame; and
a linkage connected to the frame, the linkage including:
a first link member configured to be secured to an upper leg of a patient and that is rotatable about a first link member axis to rotate the upper leg of the patient about a hip axis of a patient through an upper leg range of motion;
a second link member supported on the first link member,
wherein the second link member is configured for being secured to a lower leg of a patient, the second link member being rotatable about a second link member axis for rotating the lower leg of the patient about a knee axis of the patient through a lower leg range of motion, the second link member axis being displaceable into a selectable fixed position aligned with the knee axis and maintaining the fixed position during rotation of the second link member;
an actuator for rotating the second link member about the second link member axis; and
a controller controlling the actuator for selectively rotating the second member link member about the second link member axis through the lower leg range of motion,
wherein the first link member is independently rotatable about the first link member axis without causing the second link member to rotate about the second link member axis such that the patient's hip may be rotated without causing the patient's knee to rotate.

35. The end range of motion improving system according to claim 34, wherein the first link member includes an upper leg support.

36. The end range of motion improving system according to claim 34, wherein the second link member includes a lower leg support.

37. The end range of motion improving system according to claim 34, wherein the controller registers, at least one of:
   (i) time that the second link member has spent at a particular position, or
   (ii) force data from forces applied to the second link member.

38. The end range of motion improving system according to claim 34, wherein the controller is configured to, at least one of:
   (i) automatically hold the second link member at a particular position for a predetermined pause time,
   (ii) automatically and rotationally cycle the second link member between a first position and a second position, or
   (iii) automatically and rotationally cycle the first link member between a first position and a second position.

39. The end range of motion improving system according to claim 34, wherein the linkage further comprises one or more adjustable mechanisms to anatomically match the first link member axis to the hip axis of the patient.

40. The end range of motion improving system according to claim 34, further comprising one or more storage machines holding instructions executable by one or more logic machines configured for:
   (i) receiving a set of parameters;
   (ii) rotating the second link member based on the set of parameters;
   (iii) recording report data; and
   (iv) sending the report data to a database.

41. The end range of motion improving system according to claim 40, wherein the set of parameters includes, at least one of:
   (i) a maximum angle and a minimum angle,
   (ii) a maximum force, or
   (iii) time that the second link member is to hold a particular position.

42. The end range of motion improving system according to claim 40, wherein the instructions are executable to:
   (i) rotate the first link member independently about the first link member axis without causing the second link member to rotate about the second link member axis, or
   (ii) independently rotate the second link member about the second link member axis without causing the first link member to rotate about the first link member axis.

43. The end range of motion improving system according to claim 34, wherein the second link member is independently rotatable about the second link member axis without causing the first link member to rotate about the first link member axis.

44. The end range of motion improving system according to claim 34, wherein the second link member is rotatable about the second link member axis within a preset lower leg range of motion between about 0 degrees extension and about 135 degrees flexion.

45. The end range of motion improving system according to claim 34, wherein the first link member is rotatable about the first link member axis within a preset upper leg range of motion between about −45 degrees and about 0 degrees.

46. The end range of motion improving system according to claim 34,
   wherein the second link member is pivotably linked to the first link member via a polycentric gear system, and
   wherein the actuator for rotating the second link member and the polycentric gear system are connected such that movement of the actuator for rotating the second link member causes rotation of the polycentric gear system to rotate the second link member about the second link member axis.

47. An end range of motion improving system comprising:
   a frame configured to rest on a surface during use by a patient and remain stationary during a patient's leg motion, wherein a seat is attached to the frame; and
   a linkage connected to the frame, the linkage including:
      a first link member configured to be secured to an upper leg of a patient and that is rotatable about a first link member axis to rotate the upper leg of the patient about a hip axis of the patient through an upper leg range of motion;
      a second link member supported on the first link member and pivotably linked to the first link member via a polycentric gear system,
      the second link member configured for being secured to a lower leg of a patient and being rotatable about a second link member axis for rotating the lower leg of the patient about a knee axis of the patient through a lower leg range of motion, the second link member axis being displaceable into a selectable fixed position aligned with the knee axis and maintaining the fixed position during rotation of the second link member;
      wherein the second link member is rotatable about the second link member axis within a preset lower leg range of motion between about 0 degrees extension and about 135 degrees flexion;
      an actuator for rotating the second link member about the second link member axis, wherein the actuator for rotating the second link member and the polycentric gear system are connected such that movement of the actuator for rotating the second link member causes rotation of the polycentric gear system to rotate the second link member about the second link member axis; and
      a controller controlling the actuator for selectively rotating the second member link member about the second link member axis through the lower leg range of motion.

48. The end range of motion improving system according to claim 47, wherein the first link member includes an upper leg support.

49. The end range of motion improving system according to claim 47, wherein the second link member includes a lower leg support.

50. The end range of motion improving system according to claim 47, wherein the controller registers, at least one of:
   (i) time that the second link member has spent at a particular position, or
   (ii) force data from forces applied to the second link member.

51. The end range of motion improving system according to claim 47, wherein the controller is configured to, at least one of:
   (i) automatically hold the second link member at a particular position for a predetermined pause time,
   (ii) automatically and rotationally cycle the second link member between a first position and a second position, or
   (iii) automatically and rotationally cycle the first link member between a first position and a second position.

52. The end range of motion improving system according to claim 47, wherein the linkage further comprises one or more adjustable mechanisms to anatomically match the first link member axis to the hip axis of the patient.

53. The end range of motion improving system according to claim 47, further comprising one or more storage machines holding instructions executable by one or more logic machines configured for:
 (i) receiving a set of parameters;
 (ii) rotating the second link member based on the set of parameters;
 (iii) recording report data; and
 (iv) sending the report data to a database.

54. The end range of motion improving system according to claim 53, wherein the set of parameters includes, at least one of:
 (i) a maximum angle and a minimum angle,
 (ii) a maximum force, or
 (iii) time that the second link member is to hold a particular position.

55. The end range of motion improving system according to claim 53, wherein the instructions are executable to:
 (i) rotate the first link member independently about the first link member axis without causing the second link member to rotate about the second link member axis, or
 (ii) independently rotate the second link member about the second link member axis without causing the first link member to rotate about the first link member axis.

56. The end range of motion improving system according to claim 47, wherein the second link member is independently rotatable about the second link member axis without causing the first link member to rotate about the first link member axis such that the patient's knee may be rotated without causing the patient's hip to rotate.

57. The end range of motion improving system according to claim 47, wherein the first link member is independently rotatable about the first link member axis without causing the second link member to rotate about the second link member axis such that the patient's hip may be rotated without causing the patient's knee to rotate.

58. The end range of motion improving system according to claim 47, wherein the first link member independently rotates about the first link member axis without causing the second link member to rotate about the second link member axis, and the second link member independently rotates about the second link member axis without causing the first link member to rotate about the first link member axis.

59. The end range of motion improving system according to claim 47, wherein the first link member is rotatable about the first link member axis within a preset upper leg range of motion between about −45 degrees and about 0 degrees.

* * * * *